(12) United States Patent
Orlowski et al.

(10) Patent No.: US 6,659,938 B1
(45) Date of Patent: Dec. 9, 2003

(54) ASSEMBLY AND METHOD FOR FACILITATING PENILE ERECTION IN THE HUMAN MALE

(75) Inventors: Gerald J. Orlowski, 2402 E. Riviera Dr., Tempe, AZ (US) 85282; John M. Orlowski, Amsterdam, NY (US)

(73) Assignee: Gerald J. Orlowski, Tempe, AZ (US)

( * ) Notice: Subject to any disclaimer, the term of this patent is extended or adjusted under 35 U.S.C. 154(b) by 0 days.

(21) Appl. No.: 10/228,035

(22) Filed: Aug. 26, 2002

Related U.S. Application Data (63) Continuation-in-part of application No. 09/649,552, filed on Aug. 28, 2000, now abandoned.

(51) Int. Cl.[7] .................................................. A61F 5/00
(52) U.S. Cl. ..................................................... 600/38
(58) Field of Search ........................ 600/38–41; 601/6; 606/140, 202; 623/23.67, 23.68; 473/214; 128/881, 892

(56) References Cited

U.S. PATENT DOCUMENTS

| | | | |
|---|---|---|---|
| 2,031,870 A | * | 2/1936 | Vertuno ...................... 606/202 |
| 2,068,173 A | | 1/1937 | Galves |
| 2,943,859 A | * | 7/1960 | Koski et al. ................. 473/214 |
| 3,759,253 A | | 9/1973 | Cray |
| 4,175,554 A | * | 11/1979 | Gerow ......................... 600/38 |
| 4,202,347 A | * | 5/1980 | Sacks .......................... 600/499 |
| 4,203,432 A | | 5/1980 | Koch |
| 4,378,008 A | | 3/1983 | Osbon, Sr. |
| 4,723,538 A | | 2/1988 | Stewart et al. |
| 4,753,227 A | | 6/1988 | Yanuck, Jr. |
| 4,856,498 A | | 8/1989 | Osbon |
| 4,958,630 A | | 9/1990 | Rosenbluth et al. |
| 4,960,113 A | * | 10/1990 | Seeberg-Elverfeldt ....... 600/38 |
| 5,125,890 A | | 6/1992 | Merrill et al. |
| D330,081 S | | 10/1992 | Walsh |
| 5,234,402 A | | 8/1993 | Osbon |
| 5,246,015 A | * | 9/1993 | Baber .......................... 128/842 |
| D343,455 S | | 1/1994 | Osbon |
| 5,306,227 A | | 4/1994 | Osbon et al. |
| 5,421,808 A | | 6/1995 | Osbon et al. |

(List continued on next page.)

FOREIGN PATENT DOCUMENTS

WO     WO97/25007     7/1997

OTHER PUBLICATIONS

How to Use ErecAid System Classic, pamphlet, 1989, pp. 1–32, published by Charter Publishing Company.
WebMD with AOL Health—From the Cleveland Clinic: Your Guide to Birth Control, pp. 1–4. Dated Aug. 22, 2002.

(List continued on next page.)

*Primary Examiner*—Eric F. Winakur
(74) *Attorney, Agent, or Firm*—Michael W Goltry; Robert A Parsons; Parsons & Goltry

(57) ABSTRACT

A penile constriction ring and pump assembly wherein an inner tube is provided with a gap or groove at about 270° about a circular opening; or wherein an inner tube is provided with protrusions at about 120° and 60° about a circular central opening which protrude a distance into the circular central opening and when inflated with fluid apply pressure to the corpora cavernosa of the penis; means for automatically releasing the fluid from said inner tube responsive to a remote signal; and a method comprising pumping a pump to cause air under pressure to enter and inflate said inner tube until a firm, snug pressure is applied about the base of the penis; using an air evacuating pump to remove air from a cylindrical vacuum tube and thereby achieving an erection in said penis; and removing a cylindrical vacuum tube.

16 Claims, 6 Drawing Sheets

U.S. PATENT DOCUMENTS

| | | | |
|---|---|---|---|
| 5,462,514 A | | 10/1995 | Harris |
| 5,468,211 A | | 11/1995 | Welch |
| 5,511,551 A | * | 4/1996 | Sano et al. .................. 600/499 |
| 5,669,869 A | * | 9/1997 | Strom ......................... 600/38 |
| 5,683,383 A | | 11/1997 | Russell et al. |
| 5,695,444 A | | 12/1997 | Chaney |
| 5,823,939 A | * | 10/1998 | Tsagarakis ................... 600/38 |
| 5,951,460 A | | 9/1999 | Vollrath |
| 5,964,695 A | * | 10/1999 | Vollrath et al. ............... 600/38 |
| 5,997,470 A | | 12/1999 | Coates |

OTHER PUBLICATIONS

WebMD with AOL Health—From the Cleveland Clinic: Structure and function of the male reproductive system, pp. 1–5. Dated Aug. 22, 2002.

WebMD with AOL Health—Newly Diagnosed, pp. 1–3. Dated Aug. 22, 2002.

WebMD with AOL Health—From the Cleveland Clinic: Sexual Problems in Men, pp. 1–6. Dated Aug. 22, 2002.

* cited by examiner

FIIGURE 8

ASSEMBLY AND METHOD FOR FACILITATING PENILE ERECTION IN THE HUMAN MALE

This application is a continuation-in-part of application Ser. No. 09/649,552 filed Aug. 28, 2000, now abandoned.

FIELD OF INVENTION

This invention relates to a method and assembly for promoting and maintaining an erection in human males.

BACKGROUND OF THE INVENTION

Figure 3:
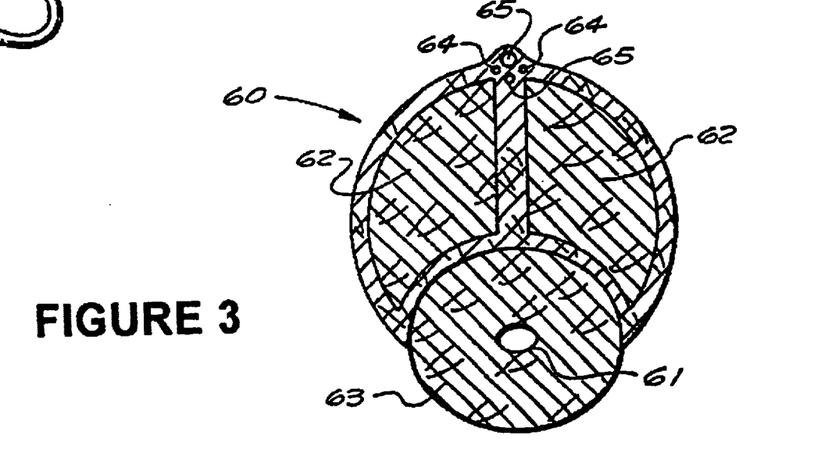
FIG. 3 is a cross-sectional view of the human penis.

The human male penis is composed mainly of erectile tissue. FIG. 3 shows a cross-sectional view of the penis. The penis is traversed by the urethra, which serves as a passage for urine and semen. The erectile tissue is divided into three bodies. The right and left corpora cavernosa traverse the dorsal length of the penis, and the corpus spongiosum, which contains the urethra, lies along the midline under the corpora cavernosa. The erectile tissue of the corpora is divided by numerous fibrous bands into many cavernous spaces, which are relatively empty when the penis is flaccid, but which become engorged with blood during an erection.

The penis is supplied with blood from the internal pudendal artery. Erection is brought about by distension of the cavernous spaces with blood, which is prevented from draining away by compression of the veins in the area.

Various means for the treatment and alleviation of impotence in males have been considered. Among the more common forms of treatment are vacuum cylinder and pump devices which evacuate a cylinder placed over the penis and thereby induce blood engorgement. For example, U.S. Pat. Nos. 4,856,498; 5,421,808; and 4,378,008 disclose vacuum devices. Once blood has been caused to engorge the penis, which causes an erection, various constriction appliances for restricting blood flow out of the penis and thereby maintaining the erection are also known. U.S. Pat. Nos. 5,306,227; 5,695,444; U.S. Pat. Nos. Des. 343,455; 5,234,402; and 3,759,253 all disclose annular elastic constriction appliances for restricting blood flow from the penis.

Although elastic annular constriction devices are useful in preventing blood flow from the penis, use of such devices can be problematic. Because the constriction devices must be sized so as to restrict blood flow, the devices must fit tightly about the base of the erect penis. Due to the tight fit and elastic nature of the devices, mounting the devices onto the penis can be painful. Consequently, it is desirable to have a nonelastic device which can constrict blood flow from the penis.

One such device is an inflatable constriction appliance as disclosed in U.S. Pat. No. 4,723,538 to Stewart et al. This patent teaches a manually inflatable constriction ring. The ring includes an outer retainer and an inner inflatable tube. The inner tube is inflated to cause constriction of the penis. Even though the Steward et al. patent does provide for more comfortable appliance for constricting blood flow from the penis, it does not provide for a manual, quick release means for instantaneously deflating the appliance.

Although the constriction device can greatly aid in obtaining an erection, the pressure of the device around the circumference of the penis can sometimes interfere with ejaculation. The ejaculate may flow out when the constriction device is removed. However, in order to maximize the pleasure associated with the sexual act, it is desirable that ejaculation occur at the point of climax. Consequently, it is desirable that the inflatable constriction device be provided with a manual quick release means so that so that the pressure within the constriction device may be instantly released at the moment of climax.

SUMMARY OF THE INVENTION

This invention relates to a method and assembly for achieving and maintaining an erection in males who cannot achieve an erection without assistance. An object of this invention is to assist impotent males achieve erection. A related type of dysfunction in men is the inability to maintain an erection for a normal length of time. This latter is a particularly troublesome situation when a condom is being used for any purpose. A loss of erection could cause a loss of benefit of the condom's function in addition to an interruption in sexual intercourse. Accordingly, it is an additional object of this invention to provide a means and method for maintaining an erection in the male.

The device of this invention is useful not only to men suffering from inability to achieve an erection, but also to men who can achieve an erection but cannot maintain it for a normal length of time. In such a case the constriction ring of this invention is applied to the penis as a first step in the method after erection has been established by normal bodily function. The pump is operated to apply pressure to maintain the desired erection and to release pressure when desired.

The present invention includes a penile constriction ring and pump assembly comprising a hollow cylindrical outer wall of relatively inelastic material, and an inner tube of elastic material positioned adjacent to said the outer wall. A central opening is defined by said inner tube for receiving the penis. A pump is operably connected to the inner tube and provides air under pressure for inflating the inner tube. A quick release valve is operably connected to the pump and instantaneously releases the pressurized air within the inner tube.

The present invention further includes a method for achieving an erection in human males comprising mounting a penile constriction ring and pump assembly of the present invention about the base of the penis. The penis is then inserted into a cylindrical vacuum tube with air evacuating pump, air is evacuated from the tube causing an erection in the penis. The pump operably connected to the inner tube is then used to inflate the tube until a firm, snug pressure is applied about said base of said penis. Once a firm erection has been obtained, the vacuum tube is removed and the user may engage in sexual intercourse. At the point of climax, the quick release valve is activated causing the instantaneous release of pressurized air from within the inner tube.

BRIEF DESCRIPTION OF THE DRAWINGS

FIG. 8 is a cross-section of the manual pump of FIG. 7 taken along the lines 8—8.

DETAILED DESCRIPTION OF THE DRAWINGS

FIG. 3 shows a cross-sectional view of the penis 60. The penis is traversed by the urethra 61, which serves as a passage for urine and semnen. The erectile tissue is divided into three bodies. The right and left corpora cavemosa 62 traverse the dorsal length of the penis, and the corpus spongiosum 63, which contains the urethra 61, lies along the midline under the corpora cavernosa 62. Dorsal arteries 64 supply blood to the penis, and dorsal veins 65 carry blood from the penis.

Figure 1:
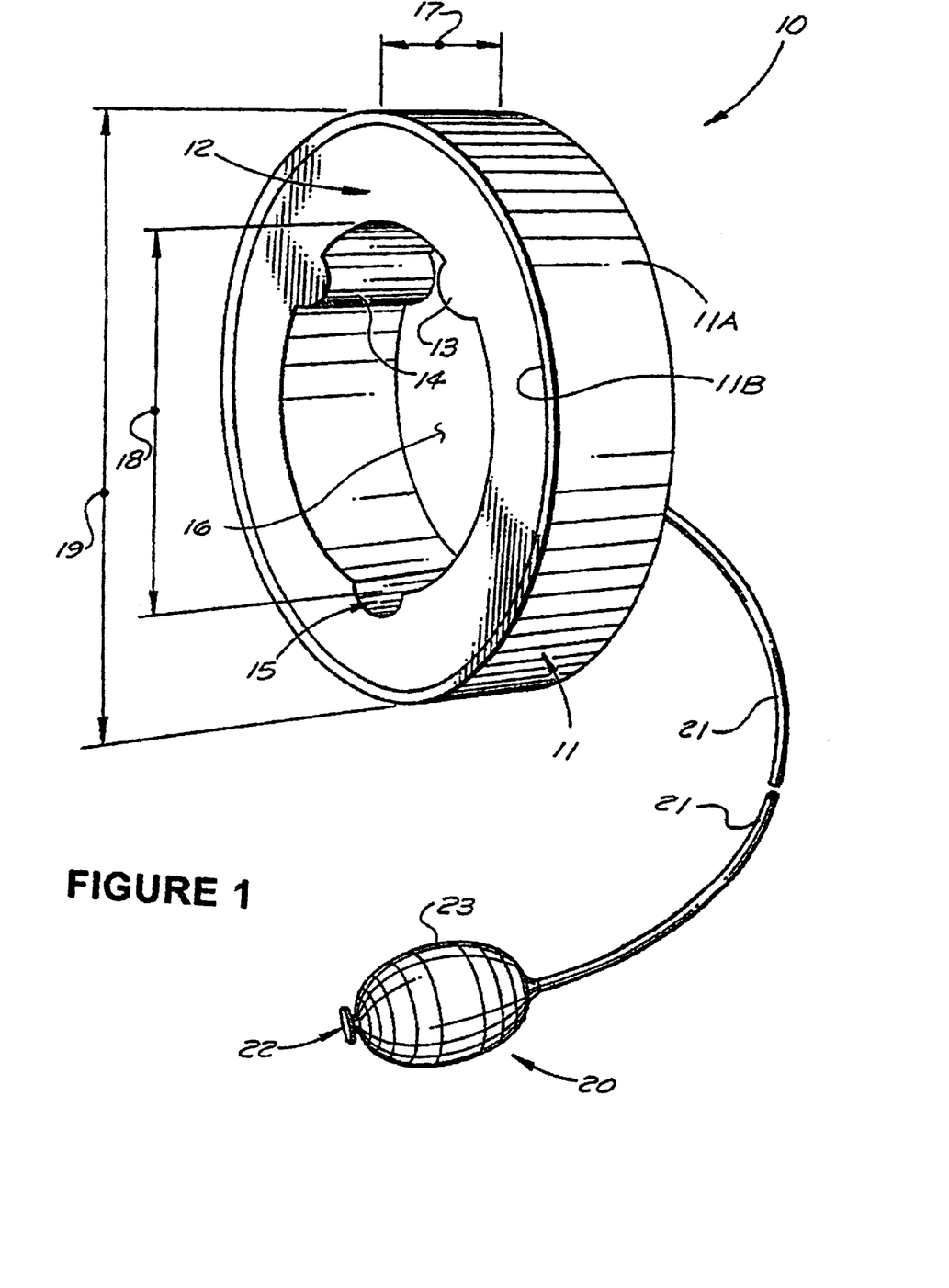
FIG. 1 is a perspective view of the air actuated constriction ring.

FIG. 1 shows the air actuated constriction ring 10 of the present invention. Ring 10 includes outer wall 11, hollow inner tube 12, and circular opening 16. Hand activated air pump 20 is operably connected with inner tube 12 by air tubing 21. Air pump 20 is provided with quick release valve 22.

Outer wall 11 is constructed of a relatively inelastic material and includes exterior surface 11A and interior surface 11B. It is preferred that wall 11 have a height 17 of about ¾ inch and an outer diameter 19 of about 2 inches.

Hollow inner tube 12 is made of an elastic material and operably connected to air pump 20. Tube 12 is positioned adjacent to interior surface 11B of wall 11 and is provided with central opening 16 having an inner diameter 18 of about 1¼ inches when not inflated. As air is pumped from air pump 20, through tubing 21 and into tube 12, the increased air pressure within the tube causes the tube to expand. Because outer wall 11 is constructed of a relatively inelastic material, tube 12 is prevented from expanding beyond outer diameter 19. Consequently, increased air pressure within tube 12 causes the tube to expand inwardly, which reduces the size of inner diameter 18 about circular central opening 16.

The upper half of inner tube 12 is provided with protrusions 13 and 14, which protrude from tube 12 into circular opening 16. Protrusions 13 and 14 should be positioned at about 120° and 60° around circular opening 16. Protrusions 13 and 14 are located adjacent to the corpora cavernosa. The additional pressure exerted by protrusions 13 and 14 further restricts blood flow from the veins in the corpora cavernosa.

The lower half of inner tube 12 is provided with groove 15. Groove 15 is located at about 270° around circular opening 16. When ring 10 is properly positioned on the penis, groove 15 is located adjacent to the urethra and corpus spongiosum. Groove 15 allows for the expansion of the corpus spongiosum during erection.

Hand activated air pump 20 includes bulbous body portion 23, tubing 21, and quick release valve 22. Tubing 21 communicates between bulbous body portion 23 and expandable inner tube 12 of air actuated constriction ring 10. Tubing 21 should be of sufficient length such that hand activate air pump 20 may be held in the hand while ring 10 is mounted about the base of the penis. By squeezing body portion 23 of pump 22 air under pressure is forced through tubing 21 and into tube 12 of ring 10. Depressing quick release valve 22 causes immediate evacuation of the air in body portion 23, tubing 21 and inner tube 12. In the preferred embodiment of the invention, quick release valve 22 is depressed at ejaculation so that the discharge of seminal fluid is not inhibited by the pressure applied by constriction ring 10.

Figure 2:
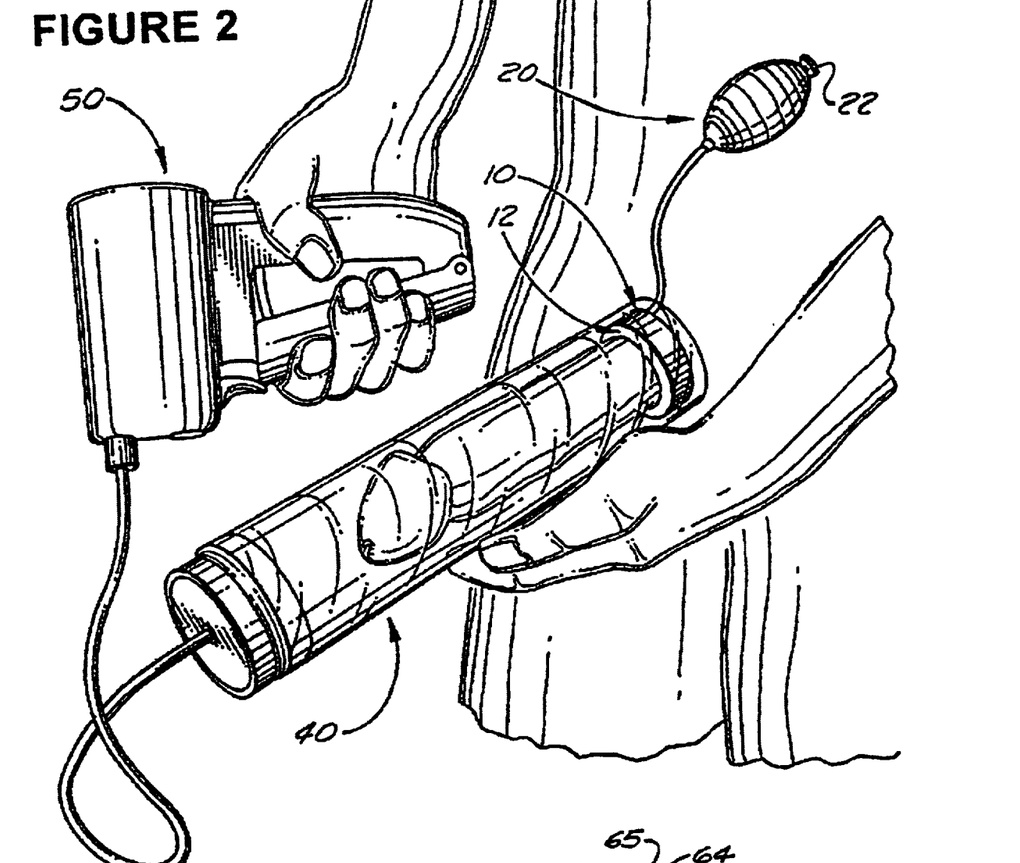
FIG. 2 is a perspective view of the air actuated constriction ring on the penis with the penis being inserted into a vacuum cylinder.

As shown in FIG. 2, the air actuated constriction ring 10 is positioned at the base of the penis. A cylindrical vacuum tube 40 with air evacuating pump 50 is then positioned over the penis. The vacuum tube 40 should be pressed snugly against ring 10 so that an air tight junction is formed between vacuum tube 40 and ring 10. Vacuum cylinders with air evacuating pumps for promoting erections are known in the art. Such devices are disclosed in U.S. Pat. No. 4,378,008 and U.S. Pat. No. 4,856,498. A suitable vacuum tube with air evacuating pump is commercially available from Osbon Medical Systems of Augusta, Georgia as the "Classic Cylinder" and "Classic Pump" stock no. 15-05.

Pump 50 is used to evacuate air from vacuum tube 40. As air is pumped from tube 40, the reduction in pressure causes blood to flow into the penis, which results in an erection. Once the desired erection has been achieved, hand activated air pump 20 is used to gradually inflate inner tube 12 of air actuated constriction ring 10. Inner tube 12 is inflated until a firm, snug pressure is applied about the base of the penis. Vacuum tube 40 can then be released and removed, and the erection is maintained. With the penis erect, the man can engage in sexual intercourse. If during intercourse the penis starts to lose the erection, the vacuum tube may be reapplied as needed.

At the moment of ejaculation, quick release valve 22 may be depressed and inner tube 12 deflated. The deflation of tube 12 releases the pressure about the base of the penis and on the corpus spongiosum and urethra Because constriction ring 10 is no longer applying pressure to the urethra, ejaculate is able to move freely through the urethra and out of the penis.

In alternate embodiment of the invention, the air actuated constriction comprises a hollow elastic tube with the outer portion of the tube being constructed of a relatively inelastic material and the inner portion of the tube being constructed of an elastic material.

Figure 4:
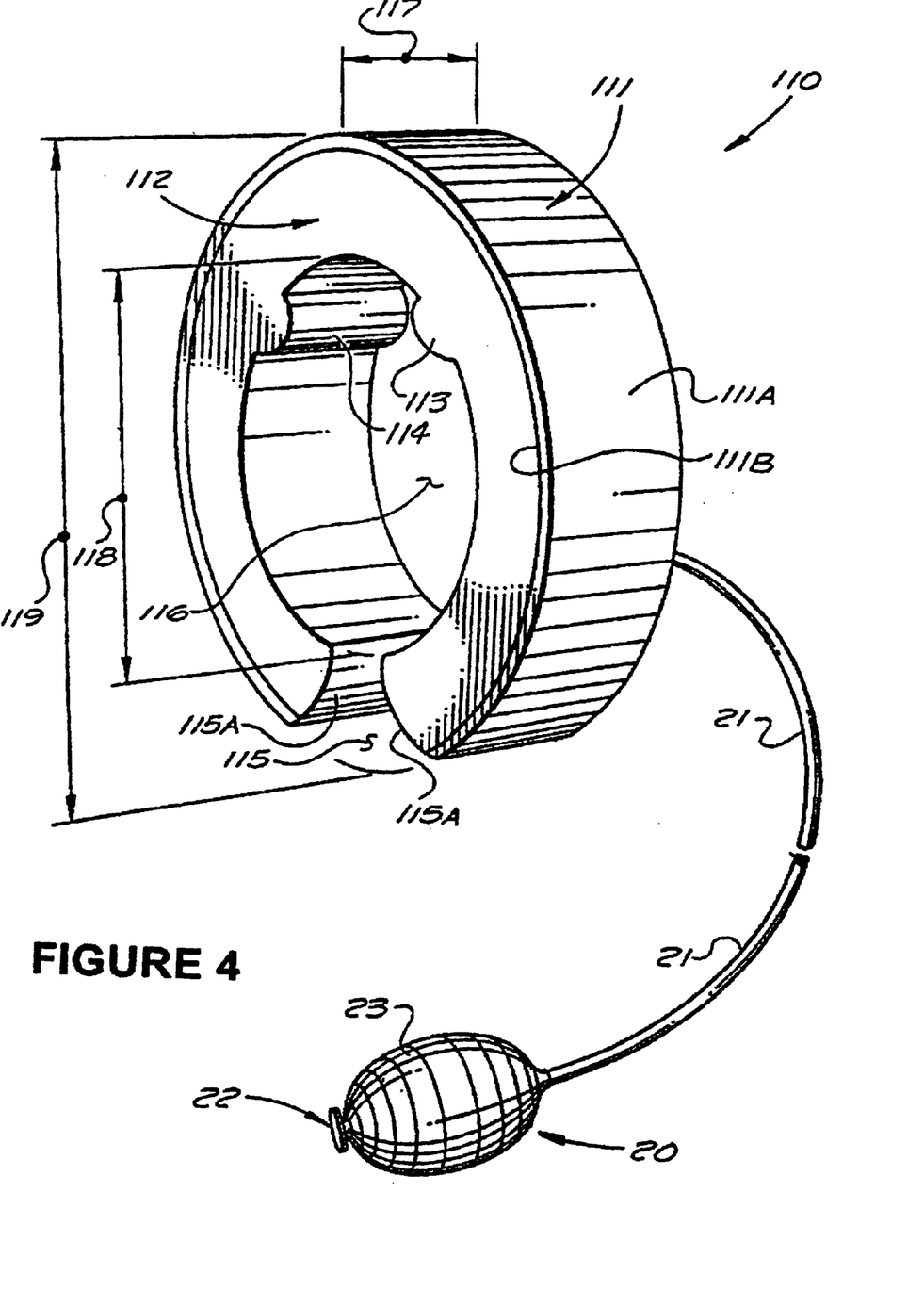
FIG. 4 is a perspective view of an alternative embodiment of the air actuated constriction ring of the present invention.

FIG. 4 shows another alternative embodiment of the air actuated constriction ring 110 of the present invention. Ring 110 includes outer wall 111, hollow inner tube 112, and opening 116. Hand activated air pump 20 is operably connected with inner tube 112 by air tubing 21. Air pump 20 is provided with quick release valve 22.

Outer wall 111 is constructed of a relatively inelastic material and includes exterior surface 111A and interior surface 111B. It is preferred that wall 111 have a height 117 of about ¾ inch and an outer diameter 119 of about 2 inches.

Hollow inner tube 112 is made of an elastic material and operably connected to air pump 20. Tube 112 is positioned adjacent to interior surface 111B of wall 111 and is provided with central opening 116 having an inner diameter 118 of about 1¼ inches when not inflated. Sizes are subject to consumer need.

The upper half of inner tube 112 is provided with protrusions 113 and 114, which protrude from tube 112 into central opening 116. Protrusions 113 and 114 should be positioned at about 120° and 60° around opening 16. Protrusions 113 and 114 are located adjacent to the corpora cavernosa.

The lower half of inner tube 112 is provided with gap 115. Gap 115 is located at about 270° around circular opening 16 and is of sufficient width so that the boundaries 115A of gap 15 are positioned on either side of the corpus spongiosum during erection of the penis. When ring 110 is properly positioned on the penis, gap 115 is positioned so that the urethra and corpus spongiosum fit within the gap. Gap 115 allows for the expansion of the corpus spongiosum during erection.

Figure 5:
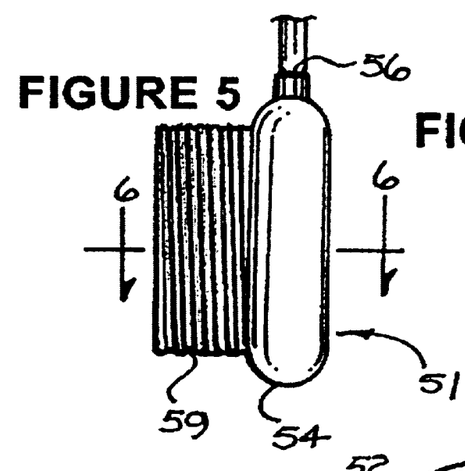
FIG. 5 is an elevation view of an alternative embodiment wherein the constriction device is incorporated into the roll of an accordion type condom.
Figure 6:
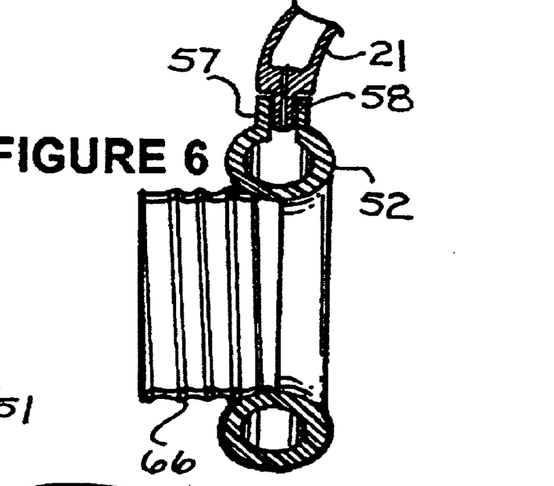
FIG. 6 is a section of FIG. 5 taken along the lines 6—6.
Figure 7:
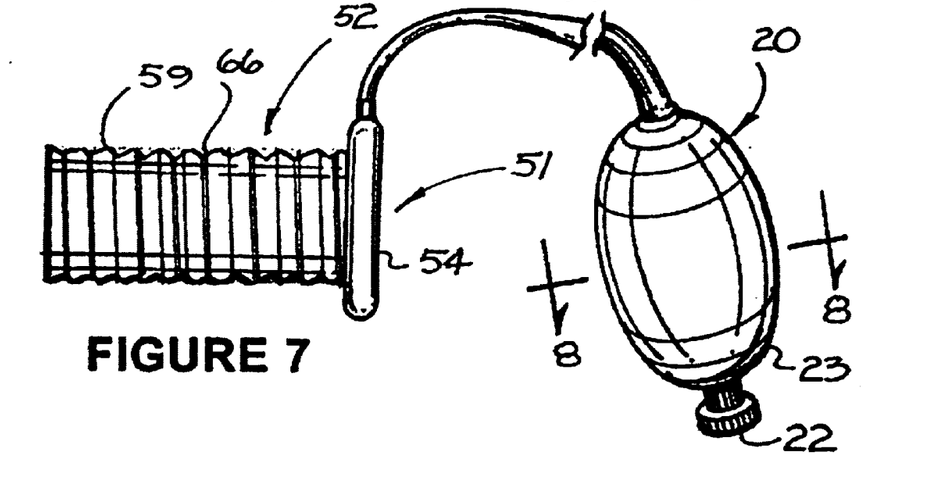
FIG. 7 is a depiction of the accordion condom, expanded, and connected to a manual pump.

When an erection has been achieved, normally, but there is doubt that it can be maintained, the assembly of FIG. 1 may be used effectively to maintain the erection. In that case, ring 10 is applied to the erect penis and the pump 20 is manually operated until the desired pressure is obtained. At a time desired by the parties, the button 22 is pressed to release the pressure. The device of FIG. 1 may be applied to the penis followed by positioning of the condom, or fitted over the condom at its base, or made integral with a condom as shown in FIGS. 5–7.

Referring now to FIGS. 5 to 10, wherein several combinations of the device shown in FIG. 1 are made integral with a condom 51, the condom 51 is provided with a lumen 52 in the roll 54 of the condom 51, said tube terminating in a one-way valve 56 constructed to receive nipple 58 disposed at the end of the tube 21 of pump 20. The nipple 58 actuates a one-way valve on removal of the tube 21. This is a smaller version of the quick release feature of the device of FIG. 1 as shown in FIG. 5a. The sheath 59 is preferably an accordion type construction 66 for ease of applying to the penis, but may also be of the roll up type. The condom 51 is disposable and is removed and discarded in the usual fashion after use.

Figure 9:
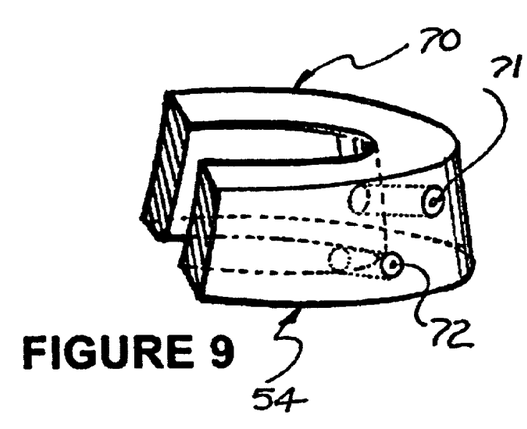
FIG. 9 is a schematic depiction of a valve useful in the invention.
Figure 10:
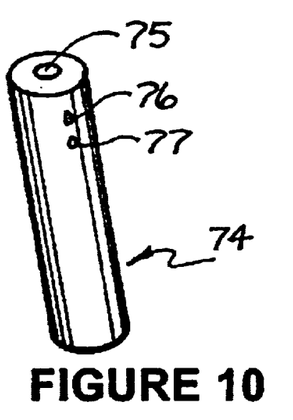
FIG. 10 is a schematic depiction of a remote control device.
Figure 11:
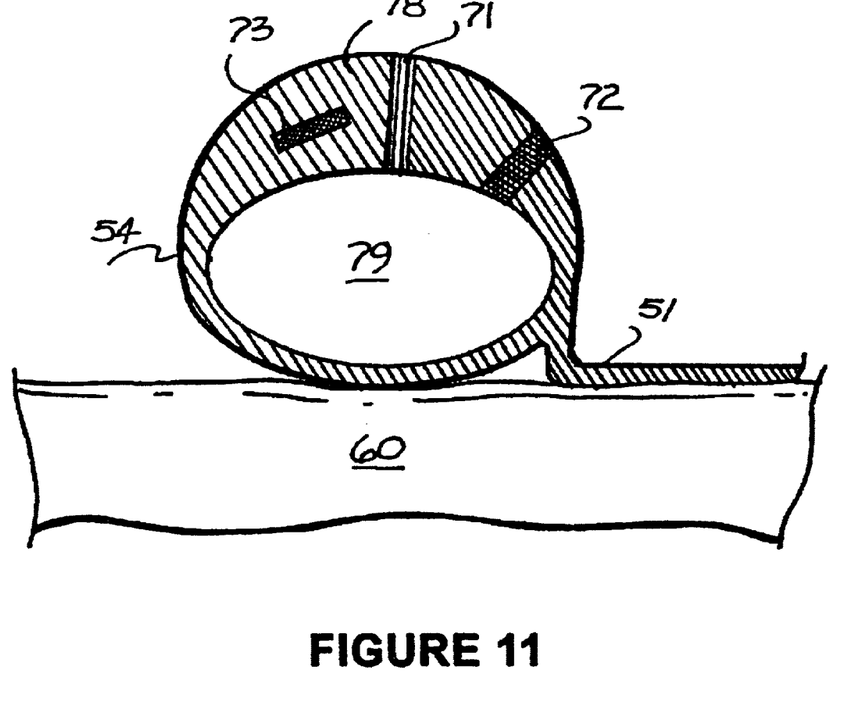
FIG. 11 is a cross-section view of a restriction ring incorporated into the roll of a condom.

Turning now to FIGS. 9–11, an alternative embodiment employing microchips and microvalves, which can be embedded in the roll of the condom 51 or provided as a separate element from the condom 51 as desired, is shown.

A portion of constriction ring 70 carries an embedded one-way valve 71 to increase pressure on the penis 60 and a second one-way valve 72 which may optionally be a small ball bearing, spring and magnet controlled by a computer chip to release pressure. Both are controlled by remote device 74 which has a signal device (not shown) controlled by release button 75 to ease the pressure of the constriction ring. Green LED indicates control ready and yellow LED indicates valve 72 is releasing pressure. A computer chip and power supply 73 may be embedded in the wall 78 to operate valves 71, 72 responsive to time, motion, or physiological changes. In FIG. 11 the constriction device is incorporated into the roll 54 of the condom 51.

Figure 12:
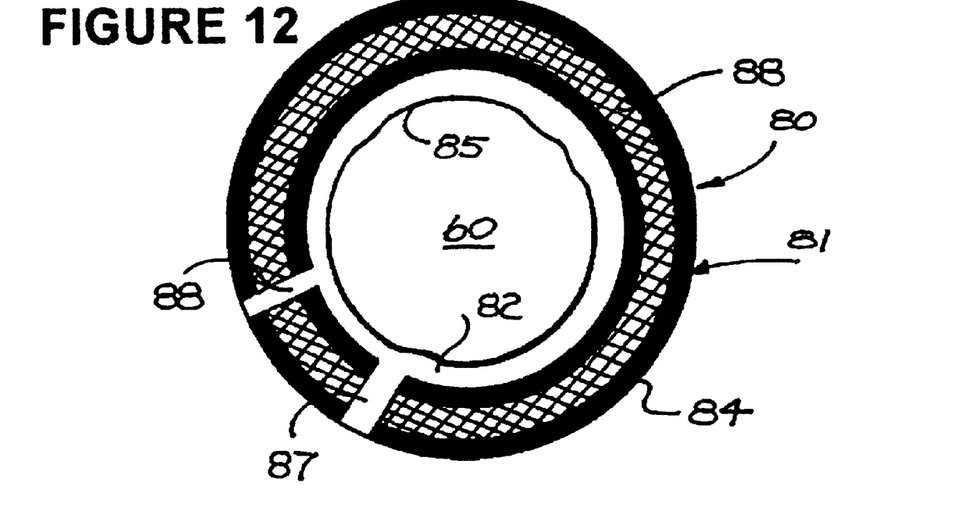
FIG. 12 is a schematic cross-section of an alternative embodiment of a constriction ring wherein a high pressure charge of air is stored in an outer tube and released to the inner tube (the inner ring) when operational.
Figure 13:
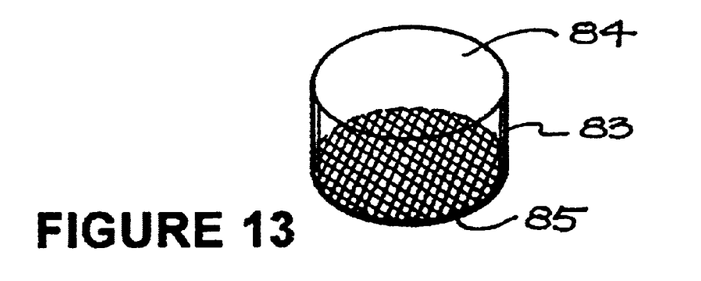
FIG. 13 is a schematicly portrayed segment of wall between the high pressure tube and the inner tube of a constriction ring.
Figure 14:
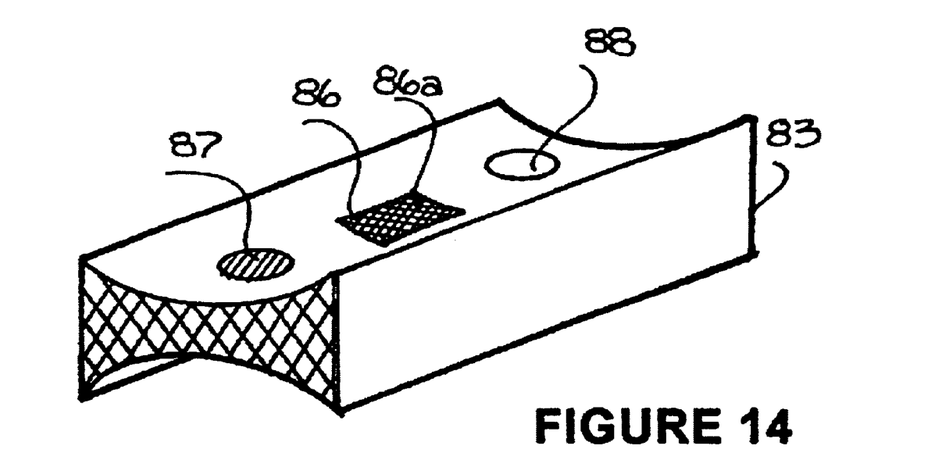
FIG. 14 is a schematic of a segment of wall between the high pressure tube and the inner tube of the constriction ring, showing the microchip controlled one-way valves and pump embedded in said wall.

Referring to FIGS. 12–14, the schematic representation of a cross-section of the constriction ring 80 is an alternative embodiment, wherein a rigid or semi-rigid outer ring 81 is charged with fluid 84, e.g. air, at high pressure and is separated from a flexible membrane low pressure inner ring 85 by a polyurethane wall 83. The wall 83 carries one-way valve 87 to inflate resiliently deformable inner ring 85 to exert pressure on the penis 60. This ring 85 may optionally have the configuration of the ring of FIG. 1 (also applies to FIGS. 5–11). A pump 88 is provided to deflate the inner ring 85 and repressurize outer ring 81. Also, microchip 86 and power supply 86a are embedded in wall 83 to make the unit completely self-contained. The chip 86 may be set to operate responsive to time or motion.

The means for automatically releasing air from an inner tube may be a simple controller device with intelligence capabilities that can open and shut valves. The receiving chip in the ring and the sending chip are considerably less complex than a television remote control. The receiving computer chip is a two function chip. Function one: allow the air to move from the higher pressure chamber to the lower pressure chamber. Function two: operate the quick release vent.

The automatic feature of the invention, whereby the release of fluid pressure, e.g., air, to relieve pressure on the penis is actuated, is responsive to various combinations of measurable physiological changes, such as motion, heart rate, bodily fluid release, skin electrical conductivity and muscle tightening. In general, the technology developed for polygraph machines can be used for this purpose. Thus, the triggering of the release of pressure on the penis can be set to be responsive to sexual climax, thus allowing the afterglow of the moment to take place without the discomfort of pressure remaining on the penis.

What is claimed is:

1. A penile constriction ring and pump assembly comprising:
   a. a hollow cylindrical outer wall of relatively inelastic material, said outer wall having an interior surface and an exterior surface;
   b. an inner tube of elastic material positioned adjacent to said interior surface of said outer wall;
   c. a circular central opening defined by said inner tube for receiving the penis;
   d. a pump operably connected to said inner tube for providing air under pressure to said tube and inflating said tube;
   e. a manual quick release valve operably connected to said pump and said inner tube for selectively and instantaneously releasing the pressurized air within said inner tube and thereby deflating said tube; and
   f. wherein said inner tube is provided with a gap at positioned for receiving the corpus spongiosum or the penis.

2. The penile constriction ring and pump assembly of claim 1 wherein said outer wall has a height of about ¾ inch.

3. The penile constriction ring and pump assembly of claim 2 wherein said outer exterior surface of said outer wall has a diameter of about 2 inches.

4. The penile constriction ring of and pump assembly claim 2 wherein said circular central opening has a diameter of about 1¼ inches when said inner tube is not inflated.

5. The assembly of claim 1 further comprising means for automatically releasing the air from said inner tube responsive to a remote signal.

6. The device of claim 1 for maintaining an erection in the human male further comprising a one way valve in said inner tube, said valve constructed to receive a nipple on the insertion end of said tube, and actuated by the removal of said nipple to prevent the escape of fluid upon removal of said nipple from said valve, and disabled by the insertion of said nipple in said valve.

7. The device of claim 1 further comprising a wall between said tubes, embedded in said wall for pumping fluid between said tubes.

8. The device of claim 7 wherein said outer tube is supplied with high pressure fluid, a valve to release said fluid to said inner tube, and a pump to return said fluid to said outer tube.

9. The device of claim 8 wherein said transport of fluid is actuated by biometric signaling means responsive to time, motion, heart rate, fluid release, muscle tightening, and other physiological changes.

10. The device of claim 9 wherein the biometric signaling means are responsive to sexual climax.

11. A method for achieving and maintaining an erection in human males comprising:
   a. mounting a penile constriction ring and pump assembly about the base of the pens, said penile constriction ring and pump assembly comprising a hollow cylindrical outer wall of relatively inelastic material, said outer wall having an interior surface and al exterior surface; an inner tube of elastic material positioned adjacent to said interior surface of said outer wall; a circular central opening defined by said inner tube for receiving said penis; a pump operably connected to said inner tube for providing air under pressure to said tube and inflating said tube; and a manual quick release valve operably connected to said pump and said inner tube for selectively and instantaneously releasing the pressurized air within said inner tube and thereby deflating said tube;
   b. inserting said penis into a cylindrical vacuum tube with air evacuating pump;
   c. pressing said vacuum tube snugly against said constriction ring so that an air tight seal is formed between said vacuum lube and said constriction ring;
   d. using said air evacuating pump to remove air from said cylindrical vacuum tube and thereby achieving an erection in said penis;
   e. pumping said pump operably connected to said inner tube to cause air under pressure to enter said inner tube and inflate said inner tube;
   f. inflating said inner tube until a firm, snug pressure is applied about said base of said penis; and
   g. removing said cylindrical vacuum tube.

12. The method of claim 11 further comprising:
   a. engaging in sexual intercourse until the point of climax; and
   b. activating said quick release valve to instantaneously release pressurized air within said inner tube and thereby deflate said tube at the point of climax.

13. The method of claim 11 further comprising releasing the air in the inner tube.

14. The method of claim 13 further comprising providing means for automatically releasing the air from said inner tube responsive to a remote signal.

15. A penile constriction ring and pump assembly comprising:
   a. a hollow cylindrical outer wall of relatively inelastic material, said outer wall having an interior surface and an exterior surface;
   b. an inner tube of elastic material positioned adjacent to said interior surface of said outer wall;
   c. a circular central opening defined by said inner tube for receiving the penis;
   d. a pump operably connected to said inner tube for providing air under pressure to said tube and inflating said tube;
   e. a manual quick release valve operably connected to said pump and said inner tube for selectively and instantaneously releasing the pressurized air within said inner tube and thereby deflating said tube; and
   f. wherein said circular central opening defined by said inner tube for receiving the penis further comprises protrusions positioned and 60° about said circular central opening which protrude a distance into said circular central opening and when inflated apply pressure to the corpora cavernosa of the penis.

16. The penile constriction ring and pump assembly of claim 15 wherein said hollow elastic tube is provided with a groove positioned about said circular central opening as a erection for receiving the corpus spongiosum of the penis.

* * * * *